(12) United States Patent
Serre et al.

(10) Patent No.: US 6,890,720 B1
(45) Date of Patent: May 10, 2005

(54) ANTIGENS DERIVED FROM FILAGGRIN AND THEIR USE FOR DIAGNOSING RHEUMATOID POLYARTHRITIS

(75) Inventors: Guy Serre, Toulouse (FR); Elisabeth Girbal-Neuhauser, Toulouse (FR); Christian Vincent, Lauzerville (FR); Michel Simon, Escalquens (FR); Mireille Sebbag, Toulouse (FR); Pascal Dalbon, Lyons (FR); Colette Jolivet-Reynaud, Bron (FR); Michel Arnaud, Villeurbane (FR); Michel Jolivet, Bron (FR)

(73) Assignee: Biomerieux, Marcy-L'Etoile (FR)

( * ) Notice: Subject to any disclaimer, the term of this patent is extended or adjusted under 35 U.S.C. 154(b) by 0 days.

(21) Appl. No.: 09/254,032

(22) PCT Filed: Sep. 1, 1997

(86) PCT No.: PCT/FR97/01541

§ 371 (c)(1),
(2), (4) Date: Apr. 26, 1999

(87) PCT Pub. No.: WO98/08946

PCT Pub. Date: Mar. 5, 1998

(30) Foreign Application Priority Data

Aug. 30, 1996 (FR) .............................. 96 10651

(51) Int. Cl.$^7$ ......................... G01N 33/53; A61K 39/00; C07K 7/06
(52) U.S. Cl. ................. 435/7.1; 424/184.1; 424/185.1; 436/506; 436/509; 436/516; 530/300; 530/330; 530/350; 530/403
(58) Field of Search .......................... 424/184.1, 185.1; 435/7.1; 436/506, 509, 516; 530/300, 330, 350, 403

(56) References Cited

U.S. PATENT DOCUMENTS 5,888,833 A * 3/1999 Serre et al. ................. 436/509

* cited by examiner

*Primary Examiner*—Robert A. Wax
(74) *Attorney, Agent, or Firm*—Alston & Bird, LLP

(57) ABSTRACT

The invention concerns an artificial antigen specifically identified by the anti-filaggrin autoantibodies present in the serum of patients suffering from rheumatoid polyarthritis, and consisting of one polypeptide comprising all or part of the sequence of one filaggrin unit or of a related molecule, in which an arginine radical has been substituted by a citrulline radical. The invention also concerns the use of this antigen for diagnosing rheumatoid polyarthritis.

19 Claims, 5 Drawing Sheets

RA Serum

AHF1 (after RA Serum)

SEQUENCE LISTING

<160> NUMBER OF SEQ ID NOS: 7

<210> SEQ ID NO 1
<211> LENGTH: 24
<212> TYPE: DNA
<213> ORGANISM: Artificial Sequence
<220> FEATURE:
<223> OTHER INFORMATION: Primer for amplification of a human filaggrin
      unit.

<400> SEQUENCE: 1
ttcctatacc aggtgagcac tcat                                              24

<210> SEQ ID NO 2
<211> LENGTH: 25
<212> TYPE: DNA
<213> ORGANISM: Artificial Sequence
<220> FEATURE:
<223> OTHER INFORMATION: Primer for amplification of a human filaggrin
      unit.

<400> SEQUENCE: 2
agaccctgaa cgtccagacc gtccc                                             25

<210> SEQ ID NO 3
<211> LENGTH: 49
<212> TYPE: PRT
<213> ORGANISM: Homo sapiens

<400> SEQUENCE: 3

```
Ser Thr Gly His Ser Gly Ser Gln His Ser His Thr Thr Gln Gly
1               5                   10                  15

Arg Ser Asp Ala Ser Arg Gly Ser Gly Ser Arg Ser Thr Ser Arg
                20                  25                  30

Glu Thr Arg Asp Gln Glu Gln Ser Gly Asp Gly Ser Arg His Ser Gly
            35                  40                  45

Ser

<210> SEQ ID NO 4
<211> LENGTH: 37
<212> TYPE: PRT
<213> ORGANISM: Homo sapiens

<400> SEQUENCE: 4

Ser Gln Asp Arg Asp Ser Gln Ala Gln Ser Glu Asp Ser Glu Arg Arg
1               5                   10                  15

Ser Ala Ser Ala Ser Arg Asn His Arg Gly Ser Ala Gln Glu Gln Ser
                20                  25                  30

Arg Asp Gly Ser Arg
            35

<210> SEQ ID NO 5
<211> LENGTH: 14
<212> TYPE: PRT
<213> ORGANISM: Homo sapiens

<400> SEQUENCE: 5

Glu Gln Ser Ala Asp Ser Ser Arg His Ser Gly Ser Gly His
1               5                   10

<210> SEQ ID NO 6
<211> LENGTH: 14
<212> TYPE: PRT
<213> ORGANISM: Homo sapiens

<400> SEQUENCE: 6

Glu Ser Ser Arg Asp Gly Ser Arg His Pro Arg Ser His Asp
1               5                   10

<210> SEQ ID NO 7
<211> LENGTH: 324
<212> TYPE: PRT
<213> ORGANISM: Homo sapiens
<220> FEATURE:
<221> NAME/KEY: VARIANT
<222> LOCATION: (3)..(3)
<223> OTHER INFORMATION: Y replaced by I
<220> FEATURE:
<221> NAME/KEY: VARIANT
<222> LOCATION: (12)..(12)
<223> OTHER INFORMATION: E replaced by D
<220> FEATURE:
<221> NAME/KEY: VARIANT
<222> LOCATION: (14)..(14)
<223> OTHER INFORMATION: S replaced by A or T
<220> FEATURE:
<221> NAME/KEY: VARIANT
<222> LOCATION: (17)..(17)
<223> OTHER INFORMATION: R replaced by Q or W
<220> FEATURE:
<221> NAME/KEY: VARIANT
<222> LOCATION: (18)..(18)
<223> OTHER INFORMATION: S replaced by A or T
<220> FEATURE:
<221> NAME/KEY: VARIANT
<222> LOCATION: (19)..(19)
<223> OTHER INFORMATION: G replaced by R,  A or V
```

```
-continued

<220> FEATURE:
<221> NAME/KEY: VARIANT
<222> LOCATION: (20)..(20)
<223> OTHER INFORMATION: T replaced by P
<220> FEATURE:
<221> NAME/KEY: VARIANT
<222> LOCATION: (23)..(23)
<223> OTHER INFORMATION: G replaced by R
<220> FEATURE:
<221> NAME/KEY: VARIANT
<222> LOCATION: (24)..(24)
<223> OTHER INFORMATION: G replaced by R
<220> FEATURE:
<221> NAME/KEY: VARIANT
<222> LOCATION: (29)..(29)
<223> OTHER INFORMATION: H replaced by R
<220> FEATURE:
<221> NAME/KEY: VARIANT
<222> LOCATION: (31)..(31)
<223> OTHER INFORMATION: E replaced by D or Q
<220> FEATURE:
<221> NAME/KEY: VARIANT
<222> LOCATION: (34)..(34)
<223> OTHER INFORMATION: R replaced by Q
<220> FEATURE:
<221> NAME/KEY: VARIANT
<222> LOCATION: (38)..(38)
<223> OTHER INFORMATION: R replaced by G
<220> FEATURE:
<221> NAME/KEY: VARIANT
<222> LOCATION: (41)..(41)
<223> OTHER INFORMATION: T replaced by A
<220> FEATURE:
<221> NAME/KEY: VARIANT
<222> LOCATION: (44)..(44)
<223> OTHER INFORMATION: E replaced by Q or D
<220> FEATURE:
<221> NAME/KEY: VARIANT
<222> LOCATION: (50)..(50)
<223> OTHER INFORMATION: H replaced by R
<220> FEATURE:
<221> NAME/KEY: VARIANT
<222> LOCATION: (51)..(51)
<223> OTHER INFORMATION: G replaced by A
<220> FEATURE:
<221> NAME/KEY: VARIANT
<222> LOCATION: (52)..(52)
<223> OTHER INFORMATION: H replaced by R
<220> FEATURE:
<221> NAME/KEY: VARIANT
<222> LOCATION: (55)..(55)
<223> OTHER INFORMATION: S replaced by P
<220> FEATURE:
<221> NAME/KEY: VARIANT
<222> LOCATION: (56)..(56)
<223> OTHER INFORMATION: S replaced by R
<220> FEATURE:
<221> NAME/KEY: VARIANT
<222> LOCATION: (57)..(57)
<223> OTHER INFORMATION: S replaced by R
<220> FEATURE:
<221> NAME/KEY: VARIANT
<222> LOCATION: (58)..(58)
<223> OTHER INFORMATION: G replaced by R
<220> FEATURE:
<221> NAME/KEY: VARIANT
<222> LOCATION: (61)..(61)
<223> OTHER INFORMATION: Q replaced by H
<220> FEATURE:
<221> NAME/KEY: VARIANT
<222> LOCATION: (63)..(63)
<223> OTHER INFORMATION: S replaced by Y
<220> FEATURE:
<221> NAME/KEY: VARIANT
<222> LOCATION: (64)..(64)
<223> OTHER INFORMATION: H replaced by Y
<220> FEATURE:
<221> NAME/KEY: VARIANT
<222> LOCATION: (65)..(65)
```

```
<223> OTHER INFORMATION: Y replaced by H
<220> FEATURE:
<221> NAME/KEY: VARIANT
<222> LOCATION: (68)..(68)
<223> OTHER INFORMATION: S replaced by L
<220> FEATURE:
<221> NAME/KEY: VARIANT
<222> LOCATION: (69)..(69)
<223> OTHER INFORMATION: V replaced by A
<220> FEATURE:
<221> NAME/KEY: VARIANT
<222> LOCATION: (70)..(70)
<223> OTHER INFORMATION: D replaced by N
<220> FEATURE:
<221> NAME/KEY: VARIANT
<222> LOCATION: (71)..(71)
<223> OTHER INFORMATION: R replaced by S
<220> FEATURE:
<221> NAME/KEY: VARIANT
<222> LOCATION: (72)..(72)
<223> OTHER INFORMATION: S replaced by T
<220> FEATURE:
<221> NAME/KEY: VARIANT
<222> LOCATION: (75)..(75)
<223> OTHER INFORMATION: S replaced by R
<220> FEATURE:
<221> NAME/KEY: VARIANT
<222> LOCATION: (78)..(78)
<223> OTHER INFORMATION: H replaced by Q
<220> FEATURE:
<221> NAME/KEY: VARIANT
<222> LOCATION: (80)..(80)
<223> OTHER INFORMATION: S replaced by T
<220> FEATURE:
<221> NAME/KEY: VARIANT
<222> LOCATION: (84)..(84)
<223> OTHER INFORMATION: S replaced by T
<220> FEATURE:
<221> NAME/KEY: VARIANT
<222> LOCATION: (92)..(92)
<223> OTHER INFORMATION: H replaced by R
<220> FEATURE:
<221> NAME/KEY: VARIANT
<222> LOCATION: (94)..(94)
<223> OTHER INFORMATION: T replaced by S, Q or H
<220> FEATURE:
<221> NAME/KEY: VARIANT
<222> LOCATION: (100)..(100)
<223> OTHER INFORMATION: A replaced by T
<220> FEATURE:
<221> NAME/KEY: VARIANT
<222> LOCATION: (103)..(103)
<223> OTHER INFORMATION: Q replaced by E or T
<220> FEATURE:
<221> NAME/KEY: VARIANT
<222> LOCATION: (105)..(105)
<223> OTHER INFORMATION: R replaced by H
<220> FEATURE:
<221> NAME/KEY: VARIANT
<222> LOCATION: (106)..(106)
<223> OTHER INFORMATION: N replaced by D
<220> FEATURE:
<221> NAME/KEY: VARIANT
<222> LOCATION: (107)..(107)
<223> OTHER INFORMATION: Q replaced by E or D
<220> FEATURE:
<221> NAME/KEY: VARIANT
<222> LOCATION: (114)..(114)
<223> OTHER INFORMATION: S replaced by T
<220> FEATURE:
<221> NAME/KEY: VARIANT
<222> LOCATION: (120)..(120)
<223> OTHER INFORMATION: R replaced by H
<220> FEATURE:
<221> NAME/KEY: VARIANT
<222> LOCATION: (126)..(126)
<223> OTHER INFORMATION: S replaced by T
<220> FEATURE:
<221> NAME/KEY: VARIANT
```

```
<222> LOCATION: (127)..(127)
<223> OTHER INFORMATION: R replaced by W or Q
<220> FEATURE:
<221> NAME/KEY: VARIANT
<222> LOCATION: (129)..(129)
<223> OTHER INFORMATION: D replaced by E
<220> FEATURE:
<221> NAME/KEY: VARIANT
<222> LOCATION: (132)..(132)
<223> OTHER INFORMATION: R replaced by G
<220> FEATURE:
<221> NAME/KEY: VARIANT
<222> LOCATION: (135)..(135)
<223> OTHER INFORMATION: Q replaced by A
<220> FEATURE:
<221> NAME/KEY: VARIANT
<222> LOCATION: (136)..(136)
<223> OTHER INFORMATION: V replaced by A or S
<220> FEATURE:
<221> NAME/KEY: VARIANT
<222> LOCATION: (137)..(137)
<223> OTHER INFORMATION: G replaced by V
<220> FEATURE:
<221> NAME/KEY: VARIANT
<222> LOCATION: (140)..(140)
<223> OTHER INFORMATION: E replaced by Q or D
<220> FEATURE:
<221> NAME/KEY: VARIANT
<222> LOCATION: (142)..(142)
<223> OTHER INFORMATION: S replaced by A or E
<220> FEATURE:
<221> NAME/KEY: VARIANT
<222> LOCATION: (144)..(144)
<223> OTHER INFORMATION: P replaced by S
<220> FEATURE:
<221> NAME/KEY: VARIANT
<222> LOCATION: (146)..(146)
<223> OTHER INFORMATION: T replaced by R
<220> FEATURE:
<221> NAME/KEY: VARIANT
<222> LOCATION: (149)..(149)
<223> OTHER INFORMATION: N replaced by R
<220> FEATURE:
<221> NAME/KEY: VARIANT
<222> LOCATION: (150)..(150)
<223> OTHER INFORMATION: Q replaced by W
<220> FEATURE:
<221> NAME/KEY: VARIANT
<222> LOCATION: (154)..(154)
<223> OTHER INFORMATION: F replaced by V
<220> FEATURE:
<221> NAME/KEY: VARIANT
<222> LOCATION: (158)..(158)
<223> OTHER INFORMATION: S replaced by R
<220> FEATURE:
<221> NAME/KEY: VARIANT
<222> LOCATION: (161)..(161)
<223> OTHER INFORMATION: Q replaced by E
<220> FEATURE:
<221> NAME/KEY: VARIANT
<222> LOCATION: (162)..(162)
<223> OTHER INFORMATION: G replaced by A
<220> FEATURE:
<221> NAME/KEY: VARIANT
<222> LOCATION: (163)..(163)
<223> OTHER INFORMATION: H replaced by Q or Y
<220> FEATURE:
<221> NAME/KEY: VARIANT
<222> LOCATION: (164)..(164)
<223> OTHER INFORMATION: S replaced by P
<220> FEATURE:
<221> NAME/KEY: VARIANT
<222> LOCATION: (170)..(170)
<223> OTHER INFORMATION: W replaced by R or H
<220> FEATURE:
<221> NAME/KEY: VARIANT
<222> LOCATION: (172)..(172)
<223> OTHER INFORMATION: G replaced by A or E
<220> FEATURE:
```

```
<221> NAME/KEY: VARIANT
<222> LOCATION: (179)..(179)
<223> OTHER INFORMATION: H replaced by R
<220> FEATURE:
<221> NAME/KEY: VARIANT
<222> LOCATION: (182)..(182)
<223> OTHER INFORMATION: A replaced by S
<220> FEATURE:
<221> NAME/KEY: VARIANT
<222> LOCATION: (183)..(183)
<223> OTHER INFORMATION: Q replaced by R or W
<220> FEATURE:
<221> NAME/KEY: VARIANT
<222> LOCATION: (186)..(186)
<223> OTHER INFORMATION: S replaced by L
<220> FEATURE:
<221> NAME/KEY: VARIANT
<222> LOCATION: (189)..(189)
<223> OTHER INFORMATION: G replaced by V
<220> FEATURE:
<221> NAME/KEY: VARIANT
<222> LOCATION: (194)..(194)
<223> OTHER INFORMATION: R replaced by G, S or T
<220> FEATURE:
<221> NAME/KEY: VARIANT
<222> LOCATION: (197)..(197)
<223> OTHER INFORMATION: Q replaced by H, D or E
<220> FEATURE:
<221> NAME/KEY: VARIANT
<222> LOCATION: (200)..(200)
<223> OTHER INFORMATION: R replaced byT
<220> FEATURE:
<221> NAME/KEY: VARIANT
<222> LOCATION: (202)..(202)
<223> OTHER INFORMATION: G replaced by S
<220> FEATURE:
<221> NAME/KEY: VARIANT
<222> LOCATION: (204)..(204)
<223> OTHER INFORMATION: G replaced by R or V
<220> FEATURE:
<221> NAME/KEY: VARIANT
<222> LOCATION: (205)..(205)
<223> OTHER INFORMATION: H replaced by Q or D
<220> FEATURE:
<221> NAME/KEY: VARIANT
<222> LOCATION: (207)..(207)
<223> OTHER INFORMATION: A replaced by S
<220> FEATURE:
<221> NAME/KEY: VARIANT
<222> LOCATION: (208)..(208)
<223> OTHER INFORMATION: D replaced by E or P
<220> FEATURE:
<221> NAME/KEY: VARIANT
<222> LOCATION: (209)..(209)
<223> OTHER INFORMATION: S replaced by V
<220> FEATURE:
<221> NAME/KEY: VARIANT
<222> LOCATION: (210)..(210)
<223> OTHER INFORMATION: S replaced by R or Q
<220> FEATURE:
<221> NAME/KEY: VARIANT
<222> LOCATION: (211)..(211)
<223> OTHER INFORMATION: R replaced by S, D or Q
<220> FEATURE:
<221> NAME/KEY: VARIANT
<222> LOCATION: (212)..(212)
<223> OTHER INFORMATION: Q replaced by D or S
<220> FEATURE:
<221> NAME/KEY: VARIANT
<222> LOCATION: (215)..(215)
<223> OTHER INFORMATION: T replaced by R
<220> FEATURE:
<221> NAME/KEY: VARIANT
<222> LOCATION: (216)..(216)
<223> OTHER INFORMATION: R replaced by H
<220> FEATURE:
<221> NAME/KEY: VARIANT
<222> LOCATION: (217)..(217)
<223> OTHER INFORMATION: H replaced by A
```

```
-continued

<220> FEATURE:
<221> NAME/KEY: VARIANT
<222> LOCATION: (218)..(218)
<223> OTHER INFORMATION: T replaced by A or E
<220> FEATURE:
<221> NAME/KEY: VARIANT
<222> LOCATION: (219)..(219)
<223> OTHER INFORMATION: Q replaced by E
<220> FEATURE:
<221> NAME/KEY: VARIANT
<222> LOCATION: (220)..(220)
<223> OTHER INFORMATION: T replaced by N or S
<220> FEATURE:
<221> NAME/KEY: VARIANT
<222> LOCATION: (223)..(223)
<223> OTHER INFORMATION: G replaced by R
<220> FEATURE:
<221> NAME/KEY: VARIANT
<222> LOCATION: (224)..(224)
<223> OTHER INFORMATION: G replaced by R
<220> FEATURE:
<221> NAME/KEY: VARIANT
<222> LOCATION: (226)..(226)
<223> OTHER INFORMATION: A replaced by T
<220> FEATURE:
<221> NAME/KEY: VARIANT
<222> LOCATION: (230)..(230)
<223> OTHER INFORMATION: H replaced by Q
<220> FEATURE:
<221> NAME/KEY: VARIANT
<222> LOCATION: (236)..(236)
<223> OTHER INFORMATION: S replaced by R
<220> FEATURE:
<221> NAME/KEY: VARIANT
<222> LOCATION: (237)..(237)
<223> OTHER INFORMATION: A replaced by P
<220> FEATURE:
<221> NAME/KEY: VARIANT
<222> LOCATION: (239)..(239)
<223> OTHER INFORMATION: D replaced by E
<220> FEATURE:
<221> NAME/KEY: VARIANT
<222> LOCATION: (244)..(244)
<223> OTHER INFORMATION: G replaced by H
<220> FEATURE:
<221> NAME/KEY: VARIANT
<222> LOCATION: (245)..(245)
<223> OTHER INFORMATION: H replaced by Y or Q
<220> FEATURE:
<221> NAME/KEY: VARIANT
<222> LOCATION: (255)..(255)
<223> OTHER INFORMATION: S replaced by A
<220> FEATURE:
<221> NAME/KEY: VARIANT
<222> LOCATION: (256)..(256)
<223> OTHER INFORMATION: G replaced by A
<220> FEATURE:
<221> NAME/KEY: VARIANT
<222> LOCATION: (257)..(257)
<223> OTHER INFORMATION: I replaced by T
<220> FEATURE:
<221> NAME/KEY: VARIANT
<222> LOCATION: (259)..(259)
<223> OTHER INFORMATION: H replaced by R
<220> FEATURE:
<221> NAME/KEY: VARIANT
<222> LOCATION: (264)..(264)
<223> OTHER INFORMATION: S replaced by T
<220> FEATURE:
<221> NAME/KEY: VARIANT
<222> LOCATION: (267)..(267)
<223> OTHER INFORMATION: R replaced by S
<220> FEATURE:
<221> NAME/KEY: VARIANT
<222> LOCATION: (269)..(269)
<223> OTHER INFORMATION: S replaced by R
<220> FEATURE:
<221> NAME/KEY: VARIANT
<222> LOCATION: (274)..(274)
```

```
-continued

<223> OTHER INFORMATION: S replaced by Y
<220> FEATURE:
<221> NAME/KEY: VARIANT
<222> LOCATION: (275)..(275)
<223> OTHER INFORMATION: S replaced by R
<220> FEATURE:
<221> NAME/KEY: VARIANT
<222> LOCATION: (280)..(280)
<223> OTHER INFORMATION: S replaced by T
<220> FEATURE:
<221> NAME/KEY: VARIANT
<222> LOCATION: (282)..(282)
<223> OTHER INFORMATION: N replaced by Q or S
<220> FEATURE:
<221> NAME/KEY: VARIANT
<222> LOCATION: (288)..(288)
<223> OTHER INFORMATION: D replaced by N
<220> FEATURE:
<221> NAME/KEY: VARIANT
<222> LOCATION: (291)..(291)
<223> OTHER INFORMATION: T replaced by S
<220> FEATURE:
<221> NAME/KEY: VARIANT
<222> LOCATION: (295)..(295)
<223> OTHER INFORMATION: S replaced by A
<220> FEATURE:
<221> NAME/KEY: VARIANT
<222> LOCATION: (296)..(296)
<223> OTHER INFORMATION: A replaced by G
<220> FEATURE:
<221> NAME/KEY: VARIANT
<222> LOCATION: (297)..(297)
<223> OTHER INFORMATION: H replaced by Q
<220> FEATURE:
<221> NAME/KEY: VARIANT
<222> LOCATION: (298)..(298)
<223> OTHER INFORMATION: G replaced by R
<220> FEATURE:
<221> NAME/KEY: VARIANT
<222> LOCATION: (301)..(301)
<223> OTHER INFORMATION: G replaced by R
<220> FEATURE:
<221> NAME/KEY: VARIANT
<222> LOCATION: (302)..(302)
<223> OTHER INFORMATION: S replaced by P
<220> FEATURE:
<221> NAME/KEY: VARIANT
<222> LOCATION: (303)..(303)
<223> OTHER INFORMATION: H replaced by R
<220> FEATURE:
<221> NAME/KEY: VARIANT
<222> LOCATION: (304)..(304)
<223> OTHER INFORMATION: Q replaced by H
<220> FEATURE:
<221> NAME/KEY: VARIANT
<222> LOCATION: (305)..(305)
<223> OTHER INFORMATION: Q replaced by E
<220> FEATURE:
<221> NAME/KEY: VARIANT
<222> LOCATION: (306)..(306)
<223> OTHER INFORMATION: S replaced by A
<220> FEATURE:
<221> NAME/KEY: VARIANT
<222> LOCATION: (311)..(311)
<223> OTHER INFORMATION: T replaced by A
<220> FEATURE:
<221> NAME/KEY: VARIANT
<222> LOCATION: (314)..(314)
<223> OTHER INFORMATION: R replaced by Q
<220> FEATURE:
<221> NAME/KEY: VARIANT
<222> LOCATION: (316)..(316)
<223> OTHER INFORMATION: R replaced by Q, A or G
<220> FEATURE:
<221> NAME/KEY: VARIANT
<222> LOCATION: (317)..(317)
<223> OTHER INFORMATION: G replaced by E
<220> FEATURE:
<221> NAME/KEY: VARIANT
```

-continued

```
<222> LOCATION: (318)..(318)
<223> OTHER INFORMATION: R replaced by T, G or S

<400> SEQUENCE: 7

Phe Leu Tyr Gln Val Ser Thr His Glu Gln Ser Glu Ser Ser His Gly
1               5                   10                  15

Arg Ser Gly Thr Ser Thr Gly Gly Arg Gln Gly Ser His His Glu Gln
            20                  25                  30

Ala Arg Asp Ser Ser Arg His Ser Thr Ser Gln Glu Gly Gln Asp Thr
        35                  40                  45

Ile His Gly His Pro Gly Ser Ser Ser Gly Gly Arg Gln Gly Ser His
    50                  55                  60

Tyr Glu Gln Ser Val Asp Arg Ser Gly His Ser Gly Ser His His Ser
65                  70                  75                  80

His Thr Thr Ser Gln Gly Arg Ser Asp Ala Ser His Gly Thr Ser Gly
                85                  90                  95

Ser Arg Ser Ala Ser Arg Gln Thr Arg Asn Gln Glu Gln Ser Gly Asp
                100                 105                 110

Gly Ser Arg His Ser Gly Ser Arg His His Glu Ala Ser Ser Arg Ala
            115                 120                 125

Asp Ser Ser Arg His Ser Gln Val Gly Gln Gly Glu Ser Ser Gly Pro
    130                 135                 140

Arg Thr Ser Arg Asn Gln Gly Ser Ser Phe Ser Gln Asp Ser Asp Ser
145                 150                 155                 160

Gln Gly His Ser Glu Asp Ser Glu Arg Trp Ser Gly Ser Ala Ser Arg
                165                 170                 175

Asn His His Gly Ser Ala Gln Glu Gln Ser Arg Asp Gly Ser Arg His
            180                 185                 190

Pro Arg Ser His Gln Glu Asp Arg Ala Gly His Gly His Ser Ala Asp
        195                 200                 205

Ser Ser Arg Gln Ser Gly Thr Arg His Thr Gln Thr Ser Ser Gly Gly
    210                 215                 220

Gln Ala Ala Ser Ser His Glu Gln Ala Arg Ser Ser Ala Gly Asp Arg
225                 230                 235                 240

His Gly Ser Gly His Gln Gln Ser Ala Asp Ser Ser Arg His Ser Gly
            245                 250                 255

Ile Gly His Gly Gln Ala Ser Ser Ala Val Arg Asp Ser Gly His Arg
            260                 265                 270

Gly Ser Ser Gly Ser Gln Ala Ser Asp Asn Glu Gly His Ser Glu Asp
        275                 280                 285

Ser Asp Thr Gln Ser Val Ser Ala His Gly Gln Ala Gly Ser His Gln
    290                 295                 300

Gln Ser His Gln Glu Ser Thr Arg Gly Arg Ser Arg Gly Arg Ser Gly
305                 310                 315                 320

Arg Ser Gly Ser
```

ANTIGENS DERIVED FROM FILAGGRIN AND THEIR USE FOR DIAGNOSING RHEUMATOID POLYARTHRITIS

The present invention relates to new preparations of antigens specifically recognized by autoantibodies specific for rheumatoid arthritis.

Rheumatoid arthritis (hereinafter abbreviated "RA") is the most frequent of the chronic inflammatory rheumatisms. It is an autoimmune disease, and the serum of affected patients contains autoantibodies of which some are specific, and may constitute a marker for this disease, allowing its diagnosis even at early stages. Research studies have therefore been carried out in order to identify antigens recognized by these antibodies, in order to obtain therefrom purified preparations which can be used in conventional immmunological diagnostic techniques.

Autoantibodies which are specifically present in patients suffering from RA and which react with a rat esophageal epithelial antigen were described for the first time by B. J. J. Young et al. in Br. Med. J. 2:97–99, (1979). These autoantibodies were at the time called "antikeratin antibodies".

During previous studies, the inventors' team obtained, from human and murine malpighian epithelia, preparations of antigens related to filaggrin and to profilaggrin, which are specifically recognized by the antibodies present in the serum of patients suffering from rheumatoid arthritis, and showed that the "antikeratin antibodies" were in fact anti-filaggrin autoantibodies (hereinafter called "AFA"). Application EP 0,511,116 describes these antigenic preparations and their use for the diagnosis of rheumatoid arthritis.

Filaggrins are a family of proteins which has been identified in various species, inter alia in humans, rats, mice, guinea pigs, at the level of the keratinizing malpighian epithelia [for a review on filaggrins, cf. DALE et al. [The Keratinocyte Handbook, Cambridge University Press, pp 323–350, (1994)]. They are derived from the dephosphorylation and from the proteolysis of a precursor, profilaggrin, which essentially consists of repeated domains of filaggrin separated by interdomain peptide segments.

The gene encoding profilaggrin is composed of repeating subunits each of which encodes a molecule of filaggrin, which are separated by portions encoding the interdomain peptide segments. All the repeating units encoding each of the human filaggrins have the same length (972 base pairs in humans); however, in humans, large (10–15%) sequence variations are observed from one subunit to another. While the majority are conservative, some of these variations induce changes in amino acids and in some cases changes in the electrical charge on the protein. Thus, human filaggrins form, independently of the post-transcriptional modifications, a heterogeneous population of molecules with a similar size but with different sequences and charges (pHi equal to 8.3±1.1) [GAN et al., Biochem. 29, p. 9432–9440 (1990)].

Profilaggrin is a protein with a high molecular weight (about 400,000 in humans) which is soluble in the presence of high salt or urea concentrations. It has a high content of basic amino acids (arginine and histidine), as well as of glycine, serine and glutamic acid. It is low in nonpolar amino acids and does not contain methionine, cysteine or tryptophan. It is highly phosphorylated on serine residues, which confers on it an isoelectric point close to neutrality.

Profilaggrin is cleaved into filaggrin units during a complex process of maturation involving dephosphorylation, followed by cleavage by proteases at the level of the interdomain segments. This cleavage first generates fragments of intermediate size, and then the functional molecules of filaggrin.

The filaggrins derived from the dephosphorylation and cleavage of profilaggrin are basic proteins whose content of amino acids is similar to that of the profilaggrins. They participate in the organization of the keratin filaments and undergo gradual maturation during which the basic arginine residues are converted to neutral citrulline residues under the action of peptidylarginine deiminase [HARDING C. R. and SCOTT, I. R., J. Mol. Biol. 170, p. 651–673 (1983)]. This causes a reduction in their affinity for the keratins from which they become detached; they are then completely degraded under the action of various proteases.

The properties of filaggrins and profilaggrins have been particularly well studied in rats, in mice and in humans. The size of profilaggrin varies, depending on the species, from 300 to 400 kD and that of the filaggrins from 27 to 64 kD.

The polymorphism observed in humans between the sequences of filaggrin units within the same profilaggrin gene does not appear in rats and mice. The filaggrins exhibit, in addition, a high inter- and intra-specific variability at the level of their sequence. This variability does not however affect their functional properties or their overall amino acid composition, and their biochemical properties. Likewise, the tissue locations of profilaggrin and of filaggrins are identical in the various mammals studied.

Continuing their studies, the inventors observed that the profilaggrin present in the keratohyalin granules of the human epidermis was not, contrary to the filaggrins, recognized by AFAs [SIMON et al. Clin. Exp. Immunol. 100, 90–98 (1995)]. They then tested the reactivity of the AFAs with recombinant filaggrin, and observed that the latter was not recognized either. On the other hand, it had been previously observed that the forms of the human epidermal filaggrins mainly recognized by the AFAs were the acido-neutral forms described by SIMON et al. [J. Clin. Invest., 92, 1387, (1993)] and in application EP 0,511,116. The fact that these acido-neutral forms correspond to a late stage of maturation of filaggrin made it possible to suppose that all or part of the post-translational modifications occurring up to this stage were involved in the formation of the epitopes recognized by the AFAs.

To verify this hypothesis, the inventors sought to reproduce in vitro, using recombinant filaggrin, these post-translational modifications in order to determine the ones which were capable of influencing the antigenicity of filaggrin.

They thus observed that in fact the citrullination of filaggrin was sufficient to generate epitopes recognized by the AFAs. Indeed, they observed, by carrying out the deimination in vitro of recombinant filaggrin, that the replacement of at least part of the arginines with citrullines allow an antigen to be obtained which is specifically recognized by the AFAs present in the serum of patients suffering from RA.

SUMMARY OF THE INVENTION

The subject of the present invention is an artificial antigen which is specifically recognized by the AFAs present in the serum of patients suffering from RA, characterized in that it consists of a recombinant or synthetic polypeptide comprising all or part of a sequence derived from that of a filaggrin unit or of a related molecule, by replacing at least one arginine residue with a citrulline residue. Preferably, an antigen in accordance with the invention comprises at least 5 consecutive amino acids, and advantageously at least 10 consecutive amino acids, including at least one citrulline, of said sequence.

For the purposes of the present invention, "filaggrin unit" is understood to mean a polypeptide whose sequence is that of the product of translation of any one of the subunits encoding a filaggrin domain of the gene for human profilaggrin or from another species, or alternatively is a consensus sequence, a theoretical sequence obtained from the sequences of the filaggrin domains.

For the purposes of the present invention, "related molecule" is understood to mean any molecule having at least one arginine residue capable of being converted to a citrulline residue under the action of a PAD (peptidylarginine deiminase); by way of example, this PAD may be a rabbit muscle PAD, as shown in the examples below. It is however within the capability of persons skilled in the art to select any other appropriate PAD by simple routine tests, by reacting it with noncitrullineated human filaggrin.

The term "peptide" as used in the present application means in particular protein or protein fragment, oligopeptide, extracted, separated or substantially isolated or synthesized, especially those obtained by chemical synthesis or by expression in a recombinant organism; any peptide in whose sequence one or more amino acids of the L series are replaced by an amino acid of the D series, or vice versa; any peptide in which at least one of the CO-NH bonds, and advantageously all the CO-NH bonds of the peptide chain is (are) replaced with one or more NH-CO bonds; any peptide in which at least one of the CO-NH bonds and advantageously all the CO-NH bonds is or are replaced by one or more NH-CO bonds, the chirality of each aminoacetyl residue, whether it is involved or not in one or more abovementioned CO-NH bonds, being either conserved or reversed in relation to the aminoacyl residues constituting a reference peptide, these compounds being also designated immunoretroids, a mimotope, and the like.

Antigens in accordance with the invention may for example be obtained by the action of PAD on natural, recombinant or synthetic peptides or proteins comprising arginine residues; they may also be obtained by peptide synthesis by directly incorporating one or more citrulline residues into the synthesized peptide.

According to a preferred embodiment of an antigen in accordance with the present invention, it consists of a polypeptide comprising all or part of the sequence corresponding to amino acids 144 to 314 of a human filaggrin unit, in which at least one arginine residue has been replaced by a citrulline residue, or alternatively all or part of the sequence corresponding to amino acids 76 to 144 of a human filaggrin unit, in which at least one arginine residue has been replaced with a citrulline residue.

An antigen in accordance with the invention may for example consist of a peptide comprising all or part of the sequence corresponding to amino acids 71 to 119 or a human filaggrin unit, in which at least one arginine residue has been replaced with a citrulline residue.

Advantageously, an antigen in accordance with the invention consists of a peptide comprising all or part of at least one sequence derived from one of the sequences identified in the sequence listing in the annex under the numbers SEQ ID NO: 3, SEQ ID NO: 5, SEQ ID NO: 6, by replacing at least one arginine residue with a citrulline residue.

The subject of the present invention is also the use of the antigens in accordance with the invention, as defined above, for the in vivo diagnosis of RA.

The present invention covers in particular antigenic compositions for diagnosing the presence of autoantibodies specific for RA in a biological sample, which compositions are characterized in that they contain at least one antigen in accordance with the invention, optionally labeled and/or conjugated with a carrier molecule.

The subject of the present invention is also a method of detecting class G autoantibodies specific for RA in a biological sample, which method is characterized in that it comprises:

bringing said biological sample into contact with at least one antigen in accordance with the invention, as defined above, under conditions allowing the formation of an antigen/antibody complex with the autoantibodies specific for RA which may be present;

detecting, by any appropriate means, the antigen/antibody complex which may be formed.

This method of detection may be carried out using a kit comprising at least one antigen according to the invention, as well as buffers and reagents appropriate for constituting a reaction medium allowing the formation of an antigen/antibody complex, and/or means for detecting said antigen/antibody complex.

Said kit may also comprise, where appropriate, reference samples, such as one or more negative sera and one or more positive sera.

The present invention will be understood more clearly with the aid of the additional description which follows, which refers to examples of preparation and use of antigens in accordance with the invention.

EXAMPLE 1

Reactivity of Sera Obtained from Patients Suffering from Rheumatoid Arthritis on Epidermal Filaggrins A piece of human epidermis is ground with the aid of a "Potter" type electric grinder in a buffer with a high urea concentration (6 M), which makes it possible to solubilize all the epidermal filaggrins.

With this epidermal extract, two-dimensional electrophoresis (8–25%) acrylamide gel in the presence of 6 M urea) is carried out; the 1st dimension corresponds to a gel isoelectrofocusing in a pH gradient ranging from 5 to 8 and the second dimension corresponds to electrophoresis under denaturing conditions, in the presence of SDS. After electrophoresis, the proteins in the gel are transferred onto nitrocellulose.

The immunological reactions are carried out according to a conventional protocol.

The nitrocellulose membrane is incubated overnight at 4° C. with a serum from a patient suffering from RA, diluted 1/2000, and then the serum immunoglobulins which have reacted with the antigens bound to the membrane are detected with the aid of a peroxidase-labeled anti-human IgG secondary antibody. The presence of the peroxidase substrate is revealed by the ECL (Enhanced ChemiLuminescence, AMERSHAM) method according to the protocol recommended by the manufacturer.

In a second stage, the same membrane is washed and then incubated for one and a half hours at 20° C. in the presence, this time, of the monoclonal antibody AHF1 described by SIMON et al. [J. Invest. Dermatol. 105, 432, (1995)] at a concentration of 0.2 µg/ml, and then of a peroxidase-labeled anti-mouse IgG secondary antibody. The reaction is revealed by the ECL method, as indicated above.

Figure 1:
FIG. 1 is an electrophoresis gel obtained according to Example 1 illustrating the reactivity of serum obtained from patients suffering from rheumatoid arthritis (RA) on epidermal filaggrins.
Figure 1:

The results are illustrated by FIG. 1:

The monoclonal antibody AHF1 recognizes isoforms of filaggrin whose pHi ranges from 5.8 to 8.5. On the other hand, only the isoforms whose pHi ranges from 5.8 to 7.4 are detected by the serum from the patient suffering from RA.

The fact that only the most acidic isoforms of filaggrins are detected makes it possible to assume that the acidification of these isoforms forms part of the post-translational modifications which would be necessary for the recognition of filaggrin by the antibodies present in the sera form patients suffering from RA.

EXAMPLE 2

In Vitro Deimination of Recombinant Filaggrin by Peptidylarginine Deiminase (PAD)

Recombinant filaggrin is produced according to the following protocol:

A DNA fragment encoding a filaggrin unit is amplified by PCR, using human genomic DNA (RAJI cells: ATCC CCL86) with the aid of the following 2 primers:

(SEQ ID NO:1) 5' primer:
5'TTCCTATACCAGGTGAGCACTCAT3'
(SEQ ID NO:2) 3' primer:
5'AGACCCTGAACGTCCAGACCGTCCC3'

The amplification product is cloned into the SmaI site of the vector pUC19. The recombinant clones are selected by verifying the presence of a 972 bp insert obtained after digestion with SacI and XbaI. This insert is then subcloned into pUC19. The insert resulting from this subcloning is then transferred into the vector pGEX (marketed by the company PHARMACIA), between the EcoRI and HindIII sites. The expression vector thus obtained expresses, in *E. coli*, filaggrin fused with glutathione S-transferase (GST), under the control of the prokaryotic Tac promoter. The synthesis of the recombinant protein is induced by addition of isopropyl-β-D-galactoside (IPTG) to the culture.

The recombinant filaggrin thus obtained will be called hereinafter: "fil-gst".

Figure 2:
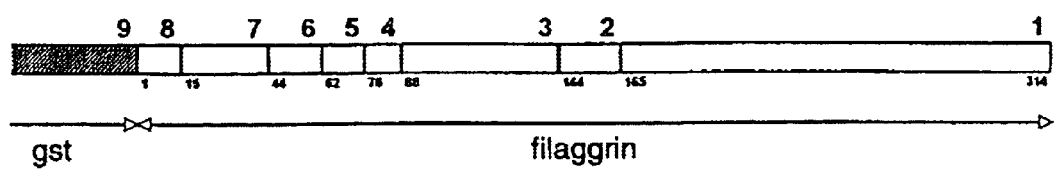
FIG. 2 illustrates the positions of the various cuts generating the fragments from post-transactional proteolysis of the full-length filaggrin.

The existence of 9 fragments which result from post-translational proteolysis of the full-length filaggrin is observed after electrophoresis. The positions of the various cuts generating these fragments are indicated in FIG. 2.

The mixture of the 9 fragments is subjected to deimination in vitro by peptidylarginine deiminase.

A rabbit muscle peptidylarginine deiminase preparation (681 U/ml) marketed by TAKARA BIOMED EUROPE is used according to the protocol recommended by the manufacturer.

The operating conditions are the following:
reaction medium: 0.1 M Tris-HCl, 10 mM $CaCl_2$, 5 mM DTT, pH 7.4;
enzyme/substrate ratio: 140 mU/µmol of filaggrin containing 10% arginine or 4 mU/µmol of arginine;
incubation: between 0 and 60 min at 50° C.;
termination of the reaction: heating 3 min in LAEMMLI buffer.

The following 8 reactions are carried out in parallel.

(1) BSA (bovine serum albumin) incubated in reaction medium (1 h, 50° C.) in PAD.

(2) BSA incubated in reaction medium (1 h, 50° C.), with 60 mU of PAD.

(3) fil-gst incubated in reaction medium (1 h, 50° C.) without PAD.

(4) fil-gst incubated in reaction medium (5 minutes at 50° C.) with 60 mU of PAD.

(5) fil-gst incubated in reaction medium (15 minutes at 50° C.) with 60 mU of PAD.

(6) fil-gst incubated in reaction medium (30 minutes at 50° C.) with 60 mU of PAD.

(7) fil-gst incubated in reaction medium (1 h at 50° C.) with 60 mU of PAD.

(8) fil-gst incubated in reaction medium (1 h at 50° C.) with 60 mU of PAD and in the presence of 10 mM N-ethylmaleimide (PAD inhibitor).

1 µl of each sample is deposited on an electrophoresis gel (PHAST®-SDS gel 12.5% PHARMACIA), and the electrophoresis is carried out with the PHAST-SYSTEM® apparatus (PHARMACIA), under the conditions recommended by the manufacturer. After transfer onto nitrocellulose, the revealing is carried out either with a pool of 5 sera from patients suffering from RA, diluted 1/2000 (FIG. 3a), or with the anti-filaggrin monoclonal antibody AHF2 [SIMON et al. J. Invest. Dermatol. 105, 432, (1995)] at the concentration of 0.2 µg/ml (FIG. 3b).

The antigen/antibody complex is revealed with the aid of a peroxidase-coupled secondary antibody by the ECL technique.

Figure 3:
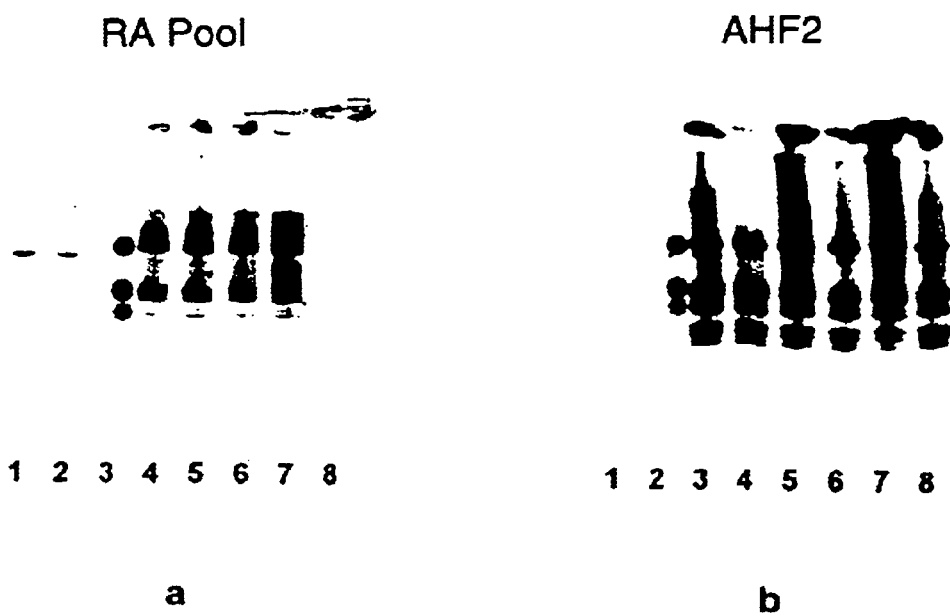
FIGS. 3a, 3b, 4a, 4b, and 5 are electrophoresis gels illustrating various experiments described in the examples that follow.

The results are illustrated by FIG. 3
Lane 1: BSA (1 hour, 50° C.)
Lane 2: BSA+PAD (1 hour, 50° C.)
Lane 3: fil-gst (1 hour, 50° C.)
Lane 4: fil-gst+PAD (15 minutes, 50° C.)
Lane 5: fil-gst+PAD (15 minutes, 50° C.)
Lane 6: fil-gst+PAD (30 minutes, 50° C.)
Lane 7: fil-gst+PAD (1 hour, 50° C.)
Lane 8: fil-gst+PAD+inhibitor (1 hour, 50° C.)

In the absence of a citrullination reaction, the fil-gst is not recognized by the sera from patients suffering from RA (FIG. 3a, lane 3), whereas from 5 minutes of citrullination (FIG. 3a, lane 4), it is detected by these sera. An increase in reactivity is observed with the pool of sera when PAD is reacted for 60 minutes at 50° C. (FIG. 3a, lane 7).

fragments 1, 2, 3 (bands identified by points) of the fil-gst are strongly recognized, after citrullination, by the sera from patients suffering from RA. Fragments 4 and 5 (bands identified by asterisks) are also recognized. These results make it possible to assume that one or more epitopes with a high affinity exist in the COOH-terminal half of filaggrin (144 to 314), this epitope being repeated between positions 76 and 144.

the monoclonal antibody AFH2 recognizes all the fragments of fil-gst, citrullinated or otherwise.

EXAMPLE 3

Specificity of the Recognition of Citrullinated Fil-gst by the Sera

Figure 4:
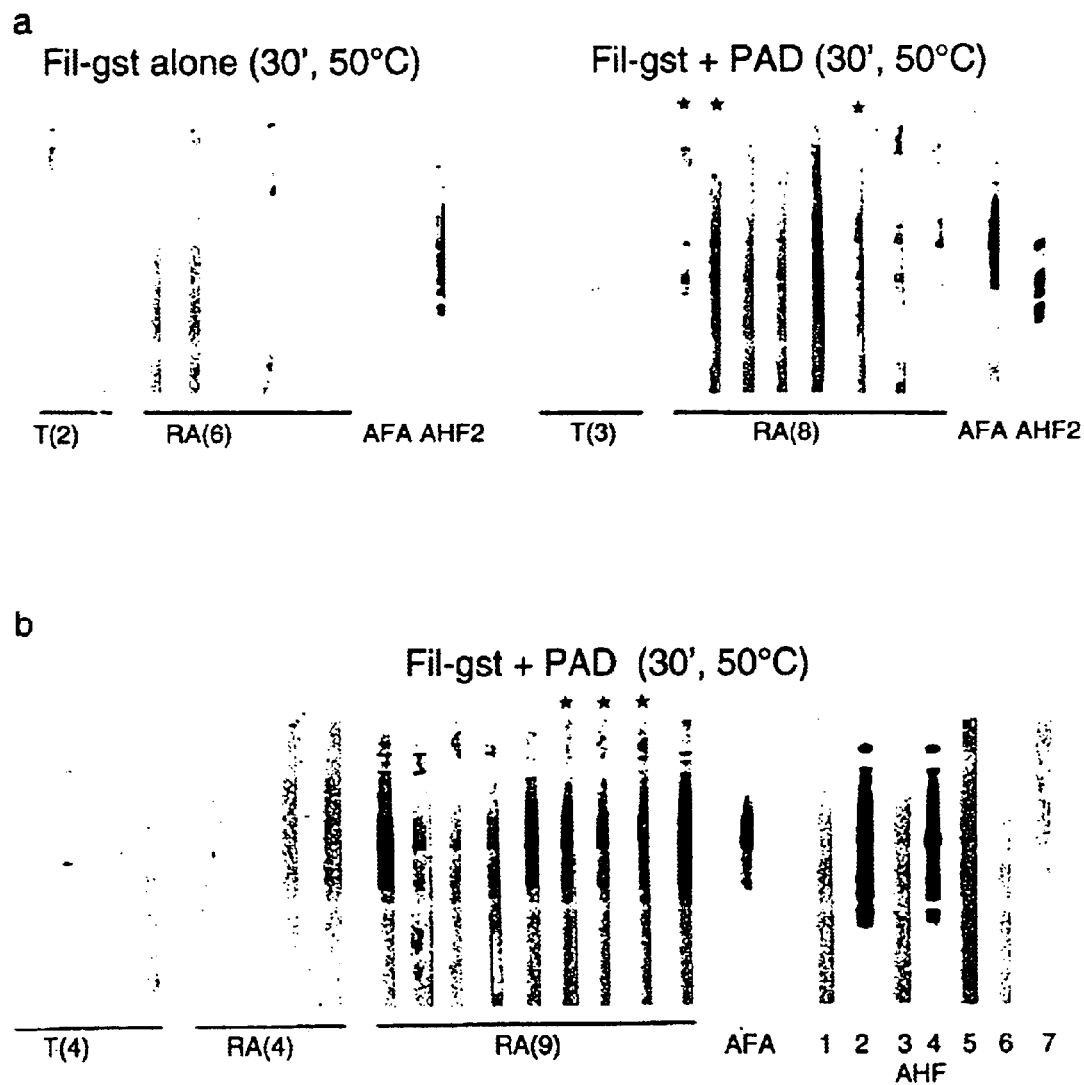

In a first series of experiments (FIG. 4a), the reactivity of noncitrullinated fil-gst (fil-gst alone, 30 minutes at 50° C.) and fil-gst citrullinated with PAD 30 minutes at 50° C. is compared with human sera composed of:

sera from normal persons: T(2) and T(3)

sera from patients suffering from RA having high AFA titers which are detected by immunotransfer on acidoneutral variants of human filaggrin, and by indirect immunofluorescence on cryosections of rat esophagus: RA(6) and RA(8);

anti-filaggrin antibodies purified from the serum from a patient suffering from RA by affinity chromatography, on a column grafted with acido-neutral isoforms of human filaggrin: AFA.

A positive control is also carried out with the monoclonal antibody AHF2.

In a second series of experiments (FIG. 4b), the reactivity of citrullinated fil-gst is confirmed with a largest series of sera:

4 control sera: T(4)

4 sera from patients suffering from RA not having AFAs detected by immunotransfer or by indirect immunofluorescence: RA(4)

9 sera from patients suffering from RA with high AFA titers (three of them (*) were also tested in the first series of experiments): RA(9)

anti-filaggrin antibodies purified by affinity chromatography, on a column grafted with the acidoneutral isoforms of filaggrin, from a pool of sera from 40 patients suffering from RA: AFA the monoclonal antibodies AHF (1–7).

The sera sere used at the dilution of 1/2000; the antifilaggrin antibodies purified by affinity chromatography are used at the concentration of 4 µg/ml; the monoclonal antibodies are used at the concentration of 0.2 µg/ml.

The results are the following:

the citrullination of recombinant filaggrin is necessary for the recognition by the AFAs of the sera from patients suffering from RA (14 positive sera out of 14 recognize it);

the antifilaggrin autoantibodies, purified by affinity chromatography from the sera from patients suffering from RA, show the same reactivity on citrullinated fil-gst as the sera from patients suffering from RA (recognition of the fragments corresponding to lanes 1 to 5). This shows that it is indeed the AFAs present in these sera which recognize the citrullinated fil-gst.

EXAMPLE 4

Citrullination of the Peptides S-47-S (SEQ ID NO:3) and S-35-R (SEQ ID NO:4) by PAD, and Test of the Reactivity of the Citrullinated Peptides The peptide of 49 amino acids S-47-S (SEQ ID NO:3) having the sequence (1-letter code):
NH2-STGHSGSQHSHTTTQGRSDASRGSSGSRSTSRET RDQEQSGDGSRHSGS-COOH corresponding to amino acids 71 to 119 of the sequence of a human filaggrin unit, and comprising 6 arginine residues, and the peptide of 37 amino acids S-35-R (SEQ ID NO:4) having the sequence (1-letter code):
NH2-SQDRDSQAQSEDSERRSASASRNHRGSAQEQSR DGSR-COOH corresponding to amino acids 155 to 191 of the sequence of a human filaggrin unit, and comprising 7 arginine residues, were prepared by peptide synthesis. The peptides S-47-R and S-35-R are represented in the sequence listing in the annex under the respective numbers SEQ ID NO: 3 and SEQ ID NO: 4.

These 2 peptides, as well as fil-gst, were citrullinated by the action of PAD, for 30 minutes at 50° C., in the same reaction medium as that indicated in Example 2. The specific conditions for each peptide, and for the fil-gst are the following:

peptide S-47-S (SEQ ID NO:3): 4 mU/µmol arginine peptide S-35-R (SEQ ID NO:4): 2.7 mU/µmol arginine fil-gst as indicated in Example 2.

The reactivity of each peptide and that of fil-gst, before and after action of the enzyme, towards the monoclonal antibody AHF4, and the serum from a patient suffering from RA, is compared by dot-blot.

The operating conditions are the following:

0.5 µg by deposition of each antigen (peptides, fil-gst, acido-neutral variants of filaggrin (AVF))

nitrocellulose treatment 45 minutes at 80° C., before immunodetection

Figure 5:
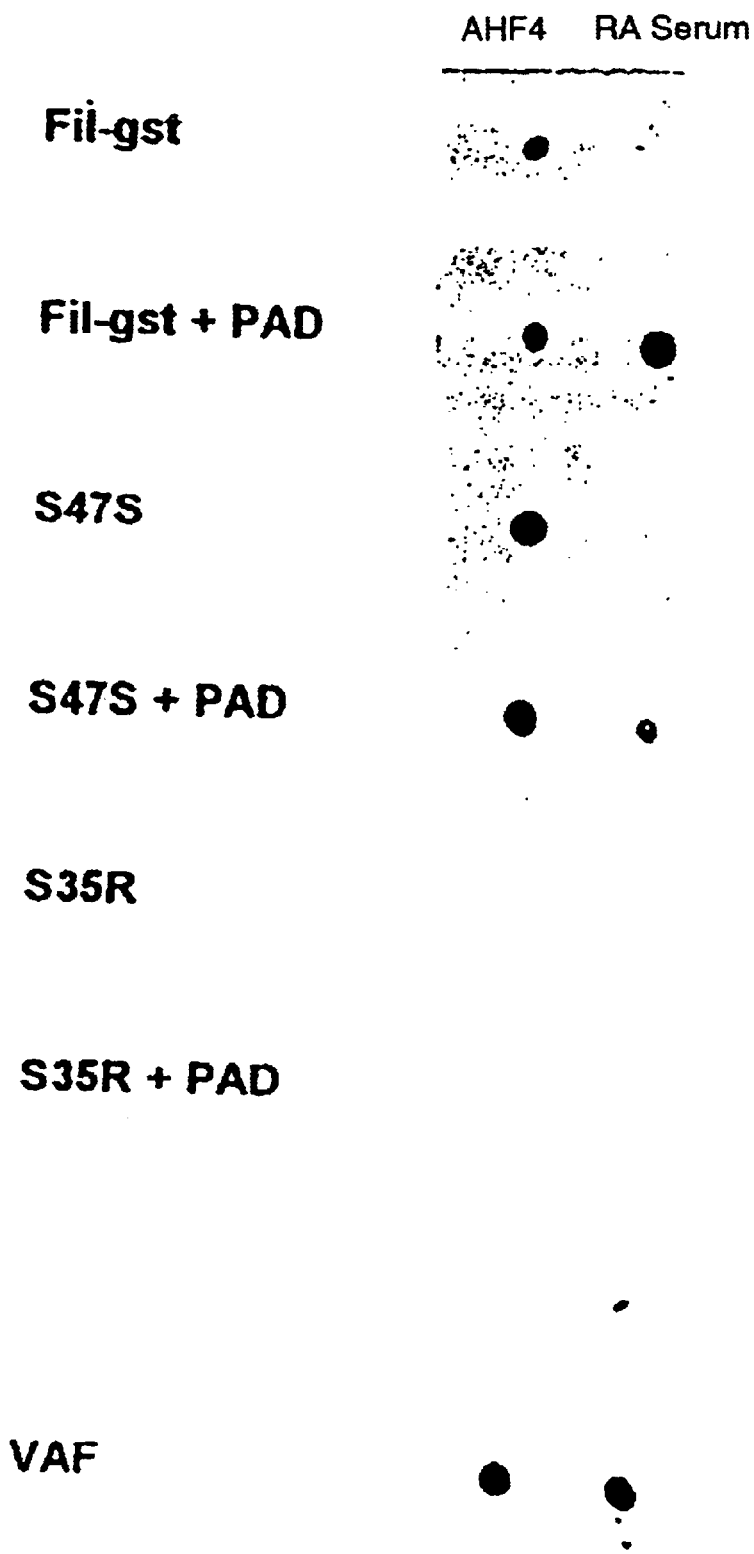

RA serum used at the dilution of 1/2000; monoclonal antibody AHF4 used at a concentration of 0.2 µg/ml The results are illustrated by FIG. 5, which shows that:

AHF4 recognizes the peptide S-47-S (SEQ ID NO:3) and fil-gst, citrullinated or not, but does not recognize S-35-R (SEQ ID NO:4), citrullinated or not.

S-47-S (SEQ ID NO:3) is recognized, after citrullination, by the serum from the patient suffering from RA, whereas S-35-R (SEQ ID NO:4), citrullinated or not, is not recognized. The same serum recognizes, moreover, the AVFs and the citrullinated fil-gst but does not recognize the noncitrullinated fil-gst.

EXAMPLE 5

Synthesis of the Peptides E-12-H (SEQ ID NO:5) and E-12-D (SEQ ID NO:6) Citrullinated and Noncitrullinated and Test of the Reactivity of the Peptides The peptides E-12-H (SEQ ID NO:5) and E-12-D (SEQ ID NO:6) were determined with reference to the nucleotide sequences of the gene for human profilaggrin which are described by GAN S. Q et al. [Biochemistry, 29: 9432–9440, (1990)].

The peptide of 14 amino acids E-12-H having the sequence (1-letter code):

NH2-EQSADSSRHSGSGH-COOH (SEQ ID NO:5)

comprises 1 arginine residue, and the peptide of 14 amino acids E-12-D having the sequence (1-letter code):

NH2-ESSRDGSRHPRSHD-COOH (SEQ ID NO:6)

comprises 3 arginine residues.

The peptides E-12-H and E-12-D are represented in the sequence listing in the annex under the respective numbers SEQ ID NO: 5 and SEQ ID NO: 6.

These peptides were prepared by solid phase peptide synthesis.

The citrullinated peptides E-12-H (SEQ ID NO:5) and E-12-D (SEQ ID NO:6) were directly synthesized by incorporation of a citrulline by replacing an arginine.

For the peptide E-12-D (SEQ ID NO:6), only the arginine residue corresponding to the $8^{th}$ amino acid of the sequence was replaced by a citrulline during peptide synthesis.

The reactivity of each citrullinated and noncitrullinated peptide was tested respectively in relation to a normal serum, to two sera from RA patients, to anti-filaggrin antibodies (AFAs) purified from a pool of 45 sera from RA patients and to anti-filaggrin antibodies purified from 12 sera from RA patients.

EXPERIMENTAL PROTOCOL

The wells of NUNC MAXISORP microtiter plates were respectively coated with the aid of the noncitrullinated and citrullinated peptides E-12-D (SEQ ID NO:6) and E-12-H (SEQ ID NO:5), diluted to a concentration of 5 µg/ml in a PBS buffer (pH: 7.4) and incubated overnight at 4° C. (final volume: 100 µg/well). The wells were saturated for 30 minutes at 37° C. in PBS-Tween 20, 0.05%, 2.5% gelatin, 200 µl/well. The negative control serum (normal serum) was diluted 1/120. The antifilaggrin antibodies were diluted in PBS-Tween 20, 0.05%–0.5% gelatin (PBS TG) such that the final anti-filaggrin autoantibody concentrations are those indicated in the accompanying Table I. The negative control serum, the RA sera and the anti-filaggrin antibodies were added (final volume: 100 µl/well) and incubated for 1 hour at 37° C. and overnight at 4° C. Peroxidase-labeled goat antibodies anti-gamma heavy chains of the human immunoglobulins (marketed by the company SOUTHERN BIOTECHNOLOGIES) were added to each well (dilution in PBSTG: 1/2000, final volume: 100 µl/well) and incubated for 1 hour at 37° C. The revealing was carried out by addition of orthophenylenediamine (2 mg/ml, for 10 minutes).

The results presented in the accompanying Table I are given as a ratio of OD at 492 nm: citrullinated peptide signal/noncitrullinated peptide signal.

These results show that in the majority of cases, the citrullinated peptide/noncitrullinated peptide OD ratio is greater than 1, and therefore illustrate the good sensitivity of the citrullinated peptides compared with the non-citrullinated peptides for their reactivity toward the anti-filaggrin autoantibodies.

TABLE 1

| Peptide | Control serum | RA1 serum | | RA2 serum | | | Pool of AFAs | | |
|---|---|---|---|---|---|---|---|---|---|
| | | 10* | 20* | 5* | 10* | 20* | 5* | 10* | 20* |
| E-12-D | 1.076 | 1.42 | 1.85 | 2.42 | 3.77 | 5.57 | 1.77 | 1.63 | 1.48 |
| E-12-H | 1 | 1.32 | 1.20 | 10.44 | 11.51 | 8.38 | 2.45 | 2.42 | 1.82 |

| | AFAs purified from 12 RA sera | | | | | | | | | | | |
|---|---|---|---|---|---|---|---|---|---|---|---|---|
| Peptide | 10* | 10* | 10* | 10* | 10* | 10* | 10* | 10* | 10* | 10* | 10* | 10* |
| E-12-D | 1.99 | 1.38 | 2.48 | 1.19 | 1.12 | 3.50 | 1.87 | 5.19 | 1.13 | 1.57 | 1.11 | 1.65 |
| E-12-H | 7.16 | 2.05 | 1.06 | 1.18 | 0.76 | 13.57 | 4.14 | 3.18 | 1.14 | 3.66 | 1.22 | 5.84 |

*Concentration of AFAs in µg/ml.

---

What is claimed is:

1. A composition consisting of an artificial antigen which is specifically recognized by the antifilaggrin autoantibodies present in the serum of patients suffering from rheumatoid arthritis, consisting of a recombinant or synthetic polypeptide having at least one citrulline residue, wherein said polypeptide is derived from any one of the filaggrin variants represented by SEQ ID NO:7 or a fragment thereof having at least 5 consecutive amino acid residues comprising at least one arginine residue.

2. The composition as claimed in claim 1, wherein said fragment of at least 5 consecutive amino acid residues of a filaggrin variant is selected from:
   fragment 144 to 314 of SEQ ID NO: 7 or sub-fragments thereof comprising at least one arginine residue; and
   fragment 76 to 144 of SEQ ID NO: 7 or sub-fragments thereof comprising at least one arginine residue.

3. The composition as claimed in claim 1, wherein said fragment of at least 5 consecutive amino acid residues of a filaggrin variant is fragment 71–119 of SEQ ID NO: 7 or sub-fragments thereof comprising at least one arginine residue.

4. The composition as claimed in claim 1, wherein said fragment of at least 5 consecutive amino acid residues of a filaggrin variant comprising at least one arginine residue is selected from peptides SEQ ID NO: 3, SEQ ID NO: 5, SEQ ID NO: 6, or sub-fragments thereof.

5. A method for the in vitro diagnosis of rheumatoid arthritis comprising the steps of:
   providing an antigen as claimed in any one of claims 1 to 4;
   providing a biological sample for diagnosis of rheumatoid arthritis;
   brining said biological sample into contact with said antigen under conditions allowing the formation of an antigen/antibody complex with the autoantibodies specific for rheumatoid arthritis which may be present in said biological sample; and
   detecting the antigen/antibody complex which may be formed.

6. An antigenic composition, which contains an antigen as claimed in any one of claims 1 to 4, with the exclusion of compositions with a structure identical to that of a preparation of isoforms of filaggrin which is purified from the human epidermis comprising a mixture of isoforms having a molecular weight of 40,000 measured by SDS-PAGE and a pI ranging between 5.8 and 7.4.

7. A method of detecting the autoantibodies specific for rheumatoid arthritis in a biological sample, which method comprises:
   brining said biological sample in contact with an antigen as claimed in any one of claims 1 to 4, under conditions allowing the formation of an antigen/antibody complex with the autoantibodies specific for rheumatoid arthritis which may be present;
   detecting, the antigen/antibody complex which may be formed.

8. A kit for the detection of autoantibodies specific for rheumatoid arthritis in a biological sample, which comprises at least one antigen as claimed in any one of claims 1 to 4, as well as buffers and reagents appropriate for constituting a reaction medium allowing the formation of an antigen/antibody complex.

9. A method of detecting the autoantibodies specific for rheumatoid arthritis in a biological sample, which method comprises:
   bringing said biological sample into contact with an antigenic composition as claimed in claim 6, under conditions allowing the formation of an antigen/antibody complex with the autoantibodies specific for rheumatoid arthritis which may be present;
   detecting the antigen/antibody complex which may be formed.

10. A kit for the detection of autoantibodies specific for rheumatoid arthritis in a biological sample, which comprises at least one antigenic composition as claimed in claim 6, as well as buffers and reagents appropriate for constituting a reaction medium allowing the formation of an antigen/antibody complex.

11. The composition of claim 6 wherein the antigen is labeled.

12. The composition of claim 6 wherein the antigen is conjugated with a carrier molecule.

13. A process for preparing an artificial antigen which is specifically recognized by the antifilaggrin autoantibodies present in the serum of patients suffering from rheumatoid arthritis, wherein said process comprises:
   providing a recombinant or synthetic polypeptide consisting of a filaggrin unit of SEQ ID NO: 7 or a fragment thereof of at least 5 consecutive amino acids comprising at least one arginine residue;
   replacing at least one arginine residue of said polypeptide with a citrulline residue; and
   recovering the citrullinated peptide recognized by the serum of patients suffering from rheumatoid arthritis.

14. A process of claim 13, wherein the replacement of arginine with citrulline is made by deimination of said arginine by a peptidylarginine deiminase.

15. A process of claim 13, wherein the replacement of arginine with citrulline is made by incorporation of one or more citrulline residues in place of one or more arginine residues during synthesis of the peptide.

16. A process for preparing an antigenic composition wherein said process comprises:
   preparing an artificial antigen by the process of claim 13; and
   incorporating said antigen into a composition.

17. A process of claim 16 further comprising labeling said artificial antigen.

18. A process of claim 16 further comprising conjugating said antigen with a carrier molecule.

19. A method for the in vitro diagnosis of rheumatoid arthritis comprising the steps of:
   preparing an artificial antigen by the process of claim 13;
   providing a biological sample for diagnosis of rheumatoid arthritis;
   bringing said biological sample into contact with said artificial antigen under conditions allowing the formation of an antigen/antibody complex with the autoantibodies specific for rheumatoid arthritis which may be present in said biological sample; and
   detecting, by any appropriate means, the antigen/antibody complex which may be formed.

* * * * *

UNITED STATES PATENT AND TRADEMARK OFFICE
CERTIFICATE OF CORRECTION

PATENT NO. : 6,890,720 B1
DATED : May 10, 2005
INVENTOR(S) : Serre et al.

Page 1 of 1

It is certified that error appears in the above-identified patent and that said Letters Patent is hereby corrected as shown below:

Title page,
Item [56], References Cited, FOREIGN PATENT DOCUMENTS, insert the following,
-- FOREIGN PATENT DOCUMENTS
WO   92 19649  11/1992
WO   89 07764  8/1989
OTHER PUBLICATIONS
"Simon, M., et al.:" "The Cytokeratin Filament-Aggregating Protein Filaggrin Is The Target Of The So-Called "Antikeratin Antibodies", Autoantibodies Specific For Rheumatoid Arthritis", The Journal Of Clinical Investigation,Vol. 92,No. 3, 1993, pages 1387-1393

Simon, M., et al.:, Monoclonal Antibodies To Human Epidermal Filaggrin, Some Not Reconizing Profilaggrin", The Journal Of Investigative Dermatology, Vol. 105, No. 3. September 1995, pages 432-437

"Gan, S-Q., et al.:" "Organization, Structure, And Polymorphisms Of The Human Profilaggrin Gene", Biochemistry, Vol. 29, 1990, pages 9432-9440 --.

Column 3,
Line 53, "119 or" should read -- 119 (SEQ ID NO:3) of --.

Signed and Sealed this

Nineteenth Day of July, 2005

JON W. DUDAS
*Director of the United States Patent and Trademark Office*